United States Patent [19]

Darchy et al.

[11] Patent Number: 5,180,414
[45] Date of Patent: Jan. 19, 1993

[54] HERBICIDAL COMPOSITIONS COMPRISING N-PHOSPHONOMETHYLGLYCINE AND ALKYL POLYOXYETHYLENE PHOSPHORIC ACID ESTER SURFACTANTS

[75] Inventors: Francois Darchy, Ste Foy Les Lyon; Jean-Claude Zobel, Lyons, both of France

[73] Assignee: Rhone-Poulenc Agrochimie, Lyons, France

[21] Appl. No.: 703,722

[22] Filed: May 21, 1991

[30] Foreign Application Priority Data

May 21, 1990 [FR] France ................. 90 06543

[51] Int. Cl.$^5$ .................. A01N 25/30; A01N 33/04; A01N 57/20
[52] U.S. Cl. .................. 504/206; 71/DIG. 1
[58] Field of Search .................. 71/86

[56] References Cited

U.S. PATENT DOCUMENTS 4,853,026 8/1989 Frisch et al. .................. 71/86
4,994,102 2/1991 Yoshido et al. .................. 71/86

FOREIGN PATENT DOCUMENTS 0252824 1/1988 European Pat. Off. .
0290416 11/1988 European Pat. Off. .

OTHER PUBLICATIONS

*Chemical Abstracts*, vol. 110, No. 25, Jun. 19, 1989, p. 228, Abstract No. 227159x.
*Derwent Central Patents Index, Basic Abstracts Journal*, wk. 46, Jan. 15, 1986, Section C: AGDOC, C01 No. 285471/46.

*Primary Examiner*—Richard L. Raymond
*Assistant Examiner*—S. Mark Clardy
*Attorney, Agent, or Firm*—Burns, Doane, Swecker & Mathis

[57] ABSTRACT

Liquid herbicidal compositions comprising aqueous solutions containing:
(a) N-phosphonomethylglycine or one of its derivatives, in the amount of at least 40 grams of glyphosate equivalent per liter of solution; and
(b) a surfactant having activating character, of the formula t,10
wherein R is an alkyl radical having 4 to 12 carbon atoms, n is an integer from 2 to 10 and M is a hydrogen, sodium, ammonium or alkylammonium.

37 Claims, No Drawings

HERBICIDAL COMPOSITIONS COMPRISING N-PHOSPHONOMETHYLGLYCINE AND ALKYL POLYOXYETHYLENE PHOSPHORIC ACID ESTER SURFACTANTS

BACKGROUND OF THE INVENTION

1. Field of the Invention

The present invention relates to new concentrated formulations based on N-phosphonomethylglycine or on compounds containing an N-phosphonomethylglycine group.

2. Description of the Prior Art

N-phosphonomethylglycine (sometimes known as glyphosate), as well as analogous compounds, their herbicidal properties and formulations containing them, are described, in particular, in U.S. Pat. No. 3,799,758. Although many water-soluble or water-insoluble glyphosate derivatives are known, it is very generally preferred, in fact, to use the water-soluble derivatives, and for this reason the salts of N-phosphonomethylglycine are the derivatives which have been generally developed or marketed, especially the isopropylammonium salt.

More recently, European Patent Application No. 290,416 describes an effort which has been made to develop concentrates based on N-phosphonomethylglycine salts, capable of containing N-phosphonomethylglycine in acid form but in any case containing this N-phosphonomethylglycine and/or its derivatives in soluble or solubilized forms, these concentrates being characterized by the presence of an alkoxylated amine of a particular type. This alkoxylated amine must have at most 12 alkoxy groups per molecule, and must have the character of a surfactant and must promote the herbicidal activity of the N-phosphonomethylglycine derivatives. It can be used in smaller amounts than the known surfactants of the previously known formulations of N-phosphonomethylglycine, at least as regards the production of concentrates intended for outdoor application, in the form of dilute slurries, on the basis of 100 to 600 l/ha.

SUMMARY OF THE INVENTION

Accordingly, an object of the present invention is to provide new compositions, or concentrated formulations (also referred to as concentrates), based on N-phosphonomethylglycine, and especially based on its water-soluble salts.

Another object of the present invention is to provide new compositions based on N-phosphonomethylglycine or its salts which are more concentrated than the known compositions.

Another object of the present invention is to provide concentrated compositions based on N-phosphonomethylglycine or its salts which are in the form of solutions.

Another object of the present invention is to provide concentrates based on N-phosphonomethylglycine or its salts which are safer, as regards toxicity to fish, than the polycondensates of ethylene oxide with amines.

Another object of the invention is to provide concentrates based on N-phosphonomethylglycine salts employing surfactants which are compatible in concentrated solutions with certain inorganic salts, and especially with those having an activating role, such as ammonium sulfate.

Another object of the invention is to provide concentrates based on N-phosphonomethylglycine or its salts comprising a high content of ammonium ($NH_4^{30}$) salt, which has an activating role.

Another object of the present invention is to provide concentrated solutions based on N-phosphonomethylglycine or its salts which are in the form of ready-to-use compositions.

Another object of the present invention is to provide concentrated compositions based on N-phosphonomethylglycine or its salts which are especially suited to controlling annual and perennial weeds.

It has now been found that these objects can be achieved wholly or partially by means of the compositions of the invention. The compositions of the invention are liquid herbicidal compositions comprising aqueous solutions containing:

(a) a herbicidally effective amount of N-phosphonomethylglycine and/or a herbicidally active derivative thereof, said amount being at least about 40 grams of glyphosate equivalent per liter of solution; and (b) an effective amount of a surfactant having an activating character of the formula:

$$R-O-(CH_2-CH_2-O)_n-P{\Large\begin{array}{c}\nearrow O-M\\ \searrow O-M\end{array}}=O$$

wherein R is an alkyl radical having 4 to 12 carbon atoms, n is an integer from 2 to 10 and M is hydrogen, sodium, ammonium or alkylammonium.

DETAILED DESCRIPTION OF THE PREFERRED EMBODIMENTS OF THE INVENTION

Here and throughout this description, except where specifically stated, percentages are percentages by weight. Moreover, wherever used herein, the expression "glyphosate equivalent" is used to denote the corresponding amount of product if all the N-phosphonomethylglycine derivative were in the form of ordinary N-phosphonomethylglycine (the acid form).

In the surfactant of the formula set forth above, R is preferably alkyl of 4 to 10 carbon atoms and n is preferably an integer from 3 to 6.

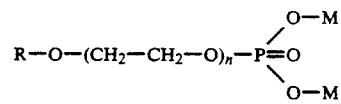

in the compositions of the invention is desirably between about 0.3 and about 6, preferably between about 0.4 and about 3.

It is also preferred that water be the only solvent present in any significant amount in the concentrated compositions of the invention.

A single surfactant of the formula set forth above may of course be replaced with a mixture of surfactants in which, on average, R and n comply with the definitions given above.

Advantageously, the concentrated compositions of the present invention comprise, in addition, one or more of the following features:

(1) The amount of N-phosphonomethylglycine present does not exceed the solubility limit of the medium in question; preferably, the amount of N-phosphonomethylglycine, expressed in terms of glyphosate equivalent, is between about 50 and about 500 g/l, and still more preferably between about 100 and about 400 g/l.

(2) The concentrated solution comprises an ammonium ($NH_4^+$) salt such as the nitrate, phosphate, sulfamate, thiocyanate or, preferably, sulfate, in an amount of from about 50 to about 400 g/l, preferably from about 100 to about 300 g/l.

(3) The pH of the aqueous solution is generally between about 3 and about 8, preferably between about 5.5 and about 7.

Due to the acidity (or alkalinity) of other constituents, it may be advantageous to adjust the pH level so that it is within the indicated ranges, in order to, for example, avoid precipitation of the N-phosphonomethylglycine. Modification of the pH level may be made by adding any kind of base, preferably isopropylamine.

The presence of N-phosphonomethylglycine, i.e. the acid form, in the compositions of the invention is, of course, possible; however, because of the low aqueous solubility of the acid form of N-phosphonomethylglycine, it may be difficult to obtain solutions having the desired high concentration of the herbicide. Therefore, a water-soluble salt of N-phosphonomethylglycine, especially the isopropylamine salt, is preferred for use in the compositions of the present invention.

The concentrated liquid compositions according to the invention are usually prepared by simply mixing the constituents.

Apart from the additives described above and used in relatively large amounts, the compositions according to the invention can contain all other kinds of components at lower doses, in particular one or more surfactants having the character of a wetting agent, formulation agents, adhesives, antifoams, corrosion inhibitors, sequestering agents, stabilizers, penetrating agents, and antifreezes.

The concentrated compositions of the invention are intended for dilution by farmers in containers containing water so that these diluted slurries can be spread on the basis of from about 100 to about 600 l/ha, the active substance, for its part, being applied on the basis of from about 0.125 to about 4.5 kg/ha.

By way of illustration, given without implied limitation, examples of solutions according to the invention, as well as examples of use of these solutions, are given below. In these examples, the active substance is N-phosphonomethylglycine in the form of the isopropylammonium salt.

EXAMPLE 1

| | |
|---|---|
| N-phosphonomethylglycine in the form of the isopropylammonium salt | 100 g/l |
| surfactant of formula $C_4H_9$—O—($CH_2$—$CH_2$—O)$_3$—P(=O) (OH)$_2$ | 300 g/l |
| isopropylamine q.s. to adjust pH to between | 6 and 7 |
| water q.s. | 1 liter |

EXAMPLE 2

| | |
|---|---|
| N-phosphonomethylglycine in the form of the isopropylammonium salt | 100 g/l |
| ammonium sulfate | 200 g/l |
| surfactant used in Example 1 | 200 g/l |
| isopropylamine q.s. to adjust pH to between | 6 and 7 |
| water q.s. | 1 liter |

EXAMPLE 3

| | |
|---|---|
| N-phosphonomethylglycine in the form of the isopropylammonium salt | 300 g/l |
| surfactant used in Example 1 | 250 g/l |
| isopropylamine q.s. to adjust pH to between | 6 and 7 |
| water q.s. | 1 liter |

EXAMPLE 4

| | |
|---|---|
| N-phosphonomethylglycine in the form of the isopropylammonium salt | 300 g/l |
| ammonium sulfate | 125 g/l |
| surfactant used in Example 1 | 125 g/l |
| isopropylamine q.s. to adjust pH to between | 6 and 7 |
| water q.s. | 1 liter |

Solutions identical to the compositions of Examples 1 to 4 have been tested regarding their physicochemical stability in the two following ways:

(1) stability after storage for one month at 50° C.;
(2) stability after storage for one month with repetitive and cyclic variations of temperature (3 days at −10° C., then 3 days at +35 ° C.) After both tests, no change was observed in the chemical composition or in the external and physical aspect.

Other solutions identical to the compositions of Examples 1 to 4 were diluted in water in the proportion of 2.5 and 5 l in 300 l; the slurries thus obtained were sprayed on various weeds. The biological/herbicidal results obtained were of the same order of magnitude as those obtained with known compositions employing condensates of ethylene oxide with amines.

While the invention has been described in terms of various preferred embodiments, the skilled artisan will appreciate that various modifications, substitutions, omissions and changes may be made without departing from the spirit thereof. Accordingly, it is intended that the scope of the present invention be limited solely by the scope of the following claims, or equivalents thereof.

What we claim is:

1. A liquid herbicidal composition comprising an aqueous solution containing:
   (a) a herbicidally effective amount of N-phosphonomethylglycine and/or a herbicidally active derivative thereof, said amount being at least about 40 grams of glyphosate equivalent per liter of solution; and
   (b) an effective amount of an activating surfactant of the formula

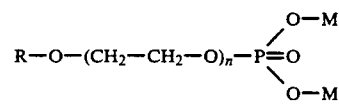

wherein R is an alkyl radical having from 4 to 12 carbon atoms, n is an integer from 2 to 10 and M is hydrogen, sodium, ammonium or alkylammonium.

2. The composition according to claim 1, wherein R is an alkyl radical having 4 to 10 carbon atoms.

3. The composition according to claim 1, wherein n is an integer from 3 to 6.

4. The composition according to claim 1, wherein R is an alkyl radical having 4 to 10 carbon atoms and n is an integer from 3 to 6.

5. The composition according to claim 4, wherein R is $C_4H_9$, n is 3 and M is hydrogen.

6. The composition according to claim 1, wherein the weight ratio $$\frac{\text{glyphosate equivalent}}{\text{surfactant}}$$

is between about 0.3 and about 6.

7. The composition according to claim 4, wherein the weight ratio $$\frac{\text{glyphosate equivalent}}{\text{surfactant}}$$

is between about 0.3 and about 6.

8. The composition according to claim 6, wherein the weight ratio is between about 0.4 and about 3.

9. The composition according to claim 7, wherein the weight ratio is between about 0.4 and about 3.

10. The composition according to claim 1, wherein the N-phosphonomethylglycine is in the form of a water-soluble salt.

11. The composition according to claim 1, wherein the N-phosphonomethylglycine is in the form of its isopropylammonium salt.

12. The composition according to claim 6, wherein the N-phosphonomethylglycine is in the form of its isopropylammonium salt.

13. The composition according to claim 7, wherein the N-phosphonomethylglycine is in the form of its isopropylammonium salt.

14. The composition according to claim 1, wherein the N-phosphonomethylglycine is present in an amount not exceeding its solubility limit in the medium, said amount, expressed as glyphosate equivalent, being between about 50 and about 500 g/l.

15. The composition according to claim 14, wherein R is an alkyl radical having 4 to 10 carbon atoms and n is an integer from 3 to 6.

16. The composition according to claim 14, wherein the weight ratio $$\frac{\text{glyphosate equivalent}}{\text{surfactant}}$$

is between about 0 3 and about 6.

17. The composition according to claim 14, wherein the N-phosphonomethylglycine is in the form of its isopropylammonium salt.

18. The composition according to claim 14, wherein the N-phosphonomethylglycine is present in an amount, expressed as glyphosate equivalent, of between about 100 and about 400 g/l.

19. The composition according to claim 18, wherein R is an alkyl radical having 4 to 10 carbon atoms and n is an integer from 3 to 6.

20. The composition according to claim 18, wherein the weight ratio $$\frac{\text{glyphosate equivalent}}{\text{surfactant}}$$

is between about 0.3 and about 6.

21. The composition according to claim 18, wherein the N-phosphonomethylglycine is in the form of its isopropylammonium salt.

22. The composition according to claim 1, further comprising from about 50 to about 400 g/l of an ammonium salt selected from the group consisting of the nitrate, phosphate, sulfamate, thiocyanate and sulfate.

23. The composition according to claim 22, wherein the N-phosphonomethylglycine is present in an amount, expressed as glyphosate equivalent, of between about 50 and about 500 g/l.

24. The composition according to claim 23, wherein R is an alkyl radical having 4 to 10 carbon atoms and n is an integer from 3 to 6.

25. The composition according to claim 23, wherein the weight ratio $$\frac{\text{glyphosate equivalent}}{\text{surfactant}}$$

about 0.3 and about 6.

26. The composition according to claim 23, wherein the N-phosphonomethylglycine is in the form of its isopropylammonium salt.

27. The composition according to claim 22, wherein the ammonium salt is ammonium sulfate.

28. The composition according to claim 22, wherein the ammonium salt is present in the amount of from about 100 to about 300 g/l.

29. The composition according to claim 28, wherein the ammonium salt is ammonium sulfate.

30. The composition according to claim 1, wherein the solvent is water.

31. The composition according to claim 1, further comprising at least one additional surfactant, said additional surfactant being a wetting agent.

32. The composition according to claim 1, further comprising one or more additives selected from the group consisting of antifoams, corrosion inhibitors, sequestering agents, stabilizers, penetrating agents and adhesives.

33. The composition according to claim 31, further comprising one or more additives selected from the group consisting of antifoams, corrosion inhibitors, sequestering agents, stabilizers, penetrating agents and adhesives.

34. The composition according to claim 1, comprising from about 5 to about 40% of herbicidal active ingredient (a), from about 0.5 to about 40% of activating surfactant (b), from about 10 to about 50% of an ammonium salt, from about 0.1 to about 10% of a wetting agent type surfactant and from about 0 to about 30% of additives.

35. The composition according to claim 1, comprising from about 10 to about 30% of herbicidal active ingredient (a), from about 10 to about 20% of activating surfactant (b) and from about 20 to about 30% of an ammonium salt.

36. A method for controlling weeds, said method comprising applying to said weeds or to the locus in which they grow a herbicidally effective amount of a composition according to claim 1.

37. A method according to claim 36, wherein said composition is diluted with water prior to application and the diluted composition is applied in an amount of from about 100 to about 600 l/ha, the active herbicidal ingredient (a) being applied in an amount of from about 0.125 to about 4.5 kg/ha.

* * * * *